United States Patent [19]
Fujiwara

[11] 4,224,529
[45] Sep. 23, 1980

[54] AUTOMATIC POLARITY CHANGING DEVICE

[75] Inventor: Toshihide Fujiwara, Fuchu, Japan

[73] Assignee: Olympus Optical Co., Ltd., Tokyo, Japan

[21] Appl. No.: 907,283

[22] Filed: May 18, 1978

[30] Foreign Application Priority Data

May 23, 1977 [JP] Japan ................................ 52-58866

[51] Int. Cl.$^2$ ..................... H01H 47/00; H01H 43/32
[52] U.S. Cl. .................................. 307/127; 361/246; 204/305
[58] Field of Search ............... 307/127, 125, 116, 138, 307/236; 361/245, 246; 204/204, 205, 211, 223, 305

[56] References Cited

U.S. PATENT DOCUMENTS

| | | | |
|---|---|---|---|
| 947,781 | 2/1910 | Babcock | 361/246 X |
| 2,558,090 | 6/1951 | Jernstedt | 204/205 |
| 2,820,157 | 1/1958 | Rieke | 361/246 X |
| 3,140,424 | 7/1964 | Stech | 361/246 |
| 3,415,726 | 12/1968 | Roller | 204/223 X |

Primary Examiner—John Gonzales
Assistant Examiner—W. J. Brady
Attorney, Agent, or Firm—Haseltine, Lake & Waters

[57] ABSTRACT

A device for automatically changing the polarity of a direct current supply source for use in a cataphoresis apparatus comprises a switch for changing the polarity of migration current, a device for generating a functional signal in response to a detection of the finish or the beginning of the migration current, a signal processing device connected to the functional signal generator for processing the functional signal to drive the polarity change switch and a polarity changing device connected between the signal processing device and the polarity change switch for instructing polarity change of the migration current to the polarity change switch and for memorizing the changed polarity of the migration current in spite of switching on or off of a power supply source. The polarity changing device always changes the polarity of the migration current to a polarity opposite to the just before polarity every detection of the finishing or the beginning of the migration current.

5 Claims, 3 Drawing Figures

AUTOMATIC POLARITY CHANGING DEVICE

BACKGROUND OF THE INVENTION

1. Field of the Invention

The present invention relates to a cataphoresis apparatus, more particularly, a device for automatically changing the polarity of a supply source for use in a cataphoresis apparatus for analyzing a serum protein by using a cellulose acetate film as a buffer solution bearing film.

2. Description of the Prior Art

A cataphoresis apparatus using a cellulose acetate film has several advantages, that is, lessening of absorption of a sample or pigment, a capability of analyzing even very small amount of the sample beause of lowering of the sample due to the lessening of adsorption of the sample, and an availability of quantitative analysis because of clear fraction due to small tailing in a cataphoretic process. An automatic cataphoretic apparatus capable of simultaneously making cataphoretic process using cellulose acetate film to the plurality of samples has been described in U.S. Pat. No. 3,999,505. Such automatic cataphoretic apparatus comprises a section for cutting a bearing film wound in a shape of a roll by a predetermined length, a section for wetting the bearing film with a buffer solution, a section for applying a serum sample on the bearing film, a cataphoretic section for fractionating the serum sample coated on the bearing film into components, a section for dyeing the bearing film which is subjected to the cataphoretic process, a section for decolorizing the dyed bearing film, a section for drying the decolorized bearing film, and a densitometer section for densitometrically processing the dryed bearing film.

The polarity of current passing through the buffer solution in a migration cell of the cataphoresis apparatus must be changed every cycle of the current flowing through the buffer solution since if do not so the ion concentration of pH of the buffer solution becomes unbalance and this unbalance affects the migration image so that the distribution curve in concentration of fractionated images and the % value of the fractions are lowered in reliability. Such change of the polarity has been realized by manual operation so that there is a tendency for the manual operator to make the changing action of the polarity erroneous because of forgetting of finally changed polarity.

SUMMARY OF THE INVENTION

An object of the present invention is to eliminate the above mentioned disadvantages of the conventional cataphoresis process.

Another object of the present invention is to provide a polarity changing device for a supply source for use in a cataphoresis apparatus in which change of the above current polarity every cycle of the current flowing through a buffer solution can automatically be performed even if the supply source of the cataphoresis apparatus is cut off on the way to cataphoresis process and the erroneous action may be prevented resulting in an elevation in reliability of measurement.

According to the present invention a device for automatically changing the polarity of a direct current supply source for use in a cataphoresis apparatus comprises a switch for changing the polarity of migration current, a device for generating a functional signal in response to a detection of the finish or the beginning of the migration current, a signal processing device connected to the functional signal generator for processing the functional signal to drive the polarity change switch and a polarity changing device connected between the signal processing device and the polarity change switch for instructing polarity change of the migration current to the polarity change switch and for memorizing the changed polarity of the migration current in spite of switching on or off of a power supply source, the polarity changing device changing the polarity of the migration current to a polarity opposite to the just previous polarity every detection of the finishing or the beginning of the migration current.

DETAILED DESCRIPTION OF THE INVENTION

Figure 1:
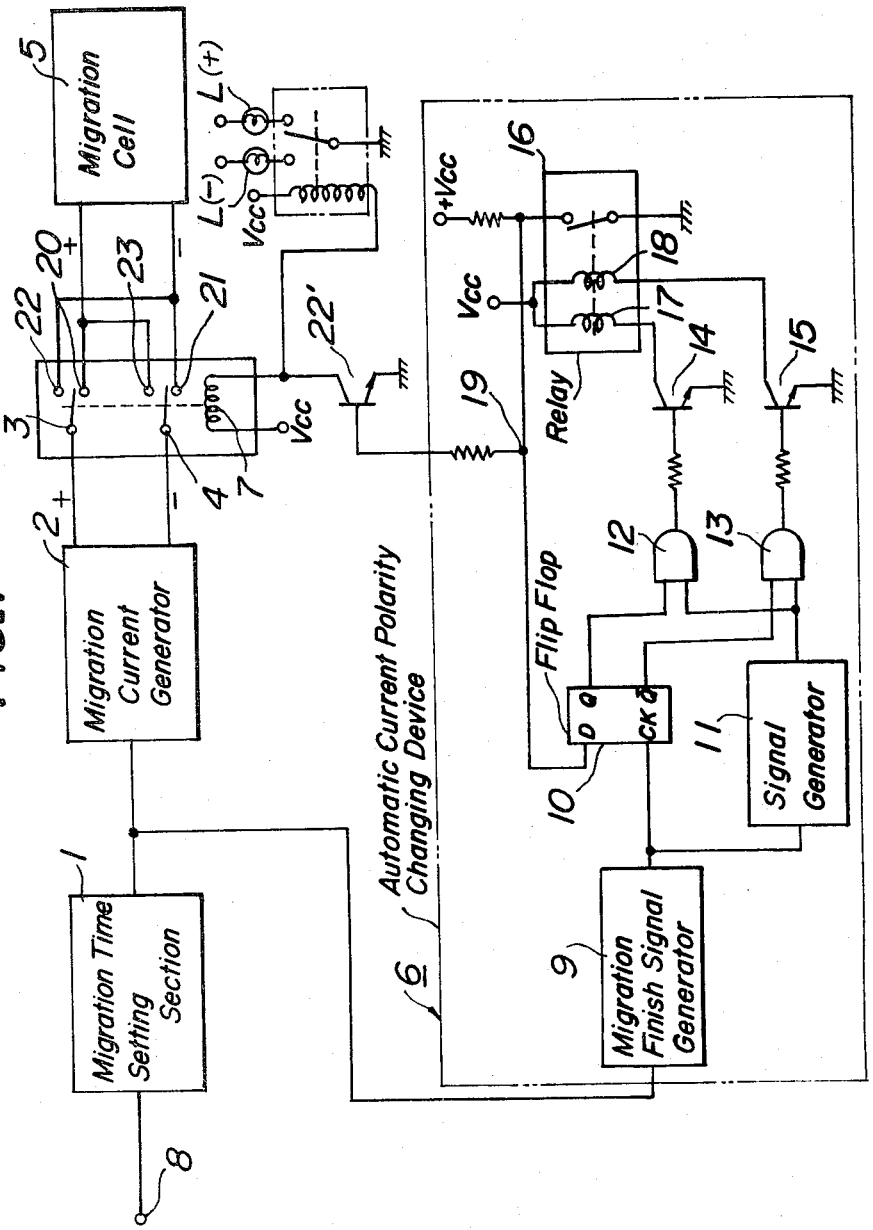
FIG. 1 is a diagrammatic view showing one embodiment of a construction of a polarity changing device according to the present invention.

Referring now to FIG. 1 there is shown a device for automatically changing the polarity of a supply source for use in a cataphoresis apparatus according to the present invention. The supply source for use in the cataphoresis apparatus comprises a migration time setting section 1, a migration current generator section 2, and a current polarity changing switch 3, 4. The output current of the polarity changing section is supplied to a migration cell 5. In the conventional process as described above the switch 3, 4 for changing the current polarity is actuated by manual operation so that the erroneous action cannot be avoided. The automatic current polarity changing device according to the present invention is shown by a block 6 in FIG. 1. In the present invention the switch 3, 4 is constructed by a relay, a current from the automatic current polarity changing device 6 is subjected to flow through a coil 7 of the relay and the coil 7 performs its contacts to change every flowing of the current resulting in an automatic change of polarity of migration current.

Figure 2:
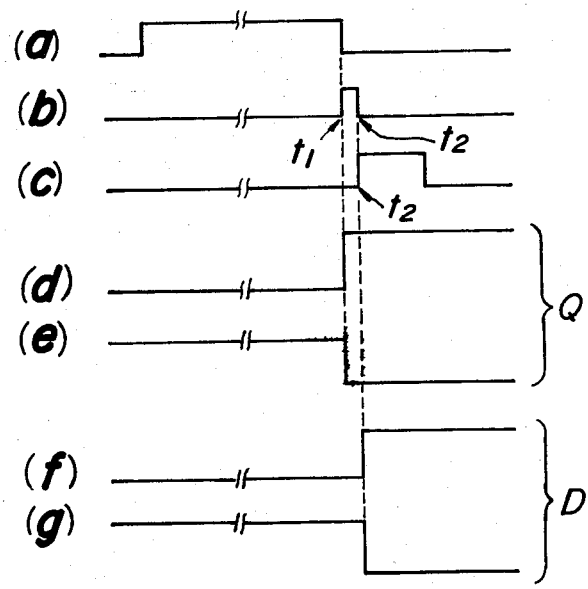
FIG. 2 is a timing chart showing signal waveforms generated in various portions of the polarity changing device shown in FIG. 1.

In operation, when an instruction signal for flowing migration current is applied to an input terminal of the cataphoresis apparatus the migration time setting section 1 operates and generates an instruction signal for generating migration current as shown in FIG. 2(a) over a preset time for example 45 minutes. The instruction signal for generating migration current is supplied to the migration current generator 2 to generate migration current during a presence of the instruction signal.

The instruction signal for generating migration current is also supplied to a migration finish signal generator 9 provided in the automatic polarity changing device 6. The generator 9 generates a finish signal of the migration current as shown in FIG. 2(b) at the end of the setting time, that is, at a fall time $t_1$ (trailing edge) of the instruction signal for generating the migration current. The finish signal is supplied to a D flip-flop 10 and a signal generator 11. The flip-flop 10 has two outputs Q and $\overline{Q}$ which are connected to first inputs of AND gates 12 and 13 respectively. The output of the signal generator 11 is connected to second inputs of the AND gates 12 and 13.

The signal generator 11 generates at a fall time $t_2$ of the input signal a signal having a predetermined duration as shown in FIG. 2(c). The AND gates 12 and 13 are opened during this duration of the signal so that the outputs Q and $\overline{Q}$ of the flip-flop 10 are supplied to switching transistors 14 and 15, respectively, to drive a relay 16 as described latter. The relay 16 is so constructed that its contact is mechanically self-maintained in any state of switching on and off to hold the state at the time of cut off even if supply source (not shown) is cut off. That is, when a coil 18 of the relay 16 is energized the contact thereof becomes an OFF state and when a coil 17 of the relay 16 is energized the contact thereof becomes an ON state. Switching on or off state of the contact is maintained even if the current flowing through the coil 17 or 18 becomes zero. For example the contact of the relay 16 maintains it's previous switching on or off state until the coil 18 is energized in the switching on state and the coil 17 is energized in the switching off state.

When the contact of the relay 16 is in a switching on state the connection point 19 has 0 level and a low level signal is supplied to the D input of the flip-flop 10 so that the flip-flop 10 is cleared by a leading edge of the output from the generator 9 and $\overline{Q}$ output of the relay 16 becomes a high level as shown in FIG. 2(d). The high level signal of the $\overline{Q}$ output is supplied to a base of the switching transistor 15 through the AND gate 13 rendering the transistor 15 an ON state so that the coil 18 is energized to make the contact of the relay 16 in an OFF state.

On the contact of the relay 16 being in OFF state the connection point 19 has a supply voltage Vcc as shown in FIG. 2(f) resulting in an ON state of a switching transistor 22' connected thereto. The transistor 22' being in ON state energizes the coil 7 of the polarity changing relay so that the switches 3 and 4 are connected to contacts 20 and 21 respectively. The output signal of the switching transistor 22', if necessary, drives a device for displaying current polarity for example lamps L(+) and L(−), etc.

In this state next cataphoresis process is performed. When the migration process is completed the migration current is ceased as described above, the generator 9 generates the migration finish signal shown in FIG. 2(b) by the trailing edge of the migration command signal shown in FIG. 2(a) and this migration finish signal is supplied to the D flip-flop 10 and the signal generator 11. In this case the contact of the relay 16 is in an OFF state, and the D terminal of the D flip-flop 10 is in a high level as shown in FIG. 2(f) so that the flip-flop 10 is set by the leading edge of the output from the generator 9 thereby to generate a high level signal in the Q output (FIG. 2(d)) and a low level signal in the $\overline{Q}$ output (FIG. 2(e)). In this case the AND gates 12 and 13 are opened by the output of the signal generator 11 and the high level signal of the Q output is supplied to the switching transistor 14 through the AND gate 12 to render the transistor 14 in an ON state so that the coil 17 is energized to make the contact of the relay 16 in an ON state. The voltage of the connection point 19 then becomes zero as shown in FIG. 2(g) and the switching transistor 22' becomes an OFF state so that the current does not flow through the coil 7. The relay contacts 3 and 4 are then switched to the contacts 22 and 23 so that the current from the migration current generator 2 is reversed its polarity and supplied to the migration cell 5.

As described above the automatic current polarity changing device according to the present invention memorizes the polarity of migration current at the time of cut off even if the supply source is cut off by using the relay in which its contact is maintained in the condition of cutting off energization so that the polarity of the migration current can always be changed with each other every current cycle in the cataphoresis process.

Figure 3:
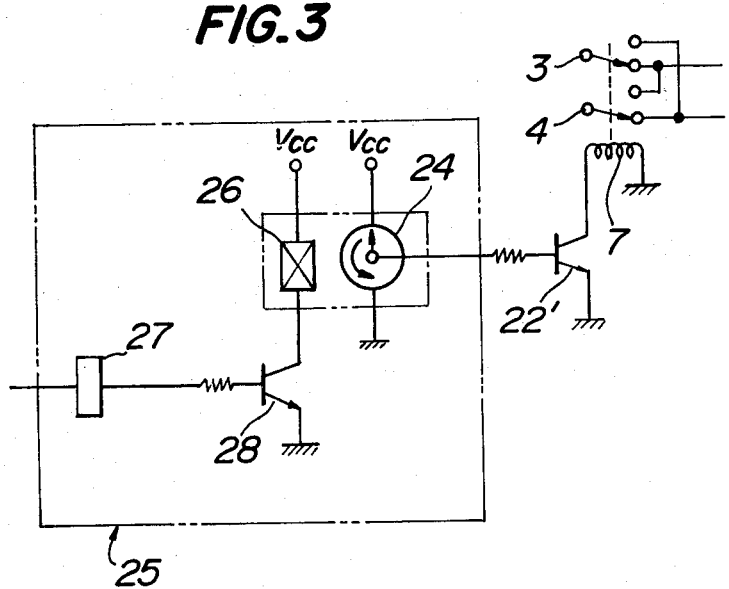
FIG. 3 is a diagrammatic view showing another embodiment of a construction of the polarity changing device according to the present invention.

It will be obvious that the present invention is not restricted to the embodiment described above, but that many variations are possible to those skilled in the art without departing from the scope of the present invention. For example, as shown in FIG. 3 the relay 16 can be replaced by a rotary switch 24. In this case the rotary switch 24 in a block 25 corresponding to the block 6 is constructed by a rotary solenoid in which every current flowing through a coil 26 the contact is rotated one by one to make the switch 24 in an ON and an OFF states repeatedly.

In this embodiment when the instruction signal for migration current on the terminal 8 is finished as in the above embodiment a migration finish signal generator 27 corresponding to the generator 9 generates a migration finish signal with same timing as that of the FIG. 2(b). This finish signal must have a duration which is a sufficiently long time to switch on a switching transistor 28. The migration finish signal is supplied to the transistor 28 to render it in an ON state resulting in an energization of a solenoid coil 26 so that the contact of the rotary switch 24 is rotated by one step thereby to supply a signal voltage having a level different from that of the signal voltage at the end of migration process to the switching transistor 22' resulting in a switching of the switch 3, 4.

This switching can supply the migration current having a different polarity every migration cycle to the migration cell 5. In this case the rotary switch 24 is so constructed that even if the power supply source is cut off the current polarity in the previous migration may mechanically be memorized to obtain alternating polarity of the current every migration cycle in spite of switching off and on of the power supply.

In the present invention polarity change of the migration current can also be realized by detecting the beginning of migration instead of detecting the finish thereof.

The polarity of migration current flowing through the buffer solution in the migration cell for use in the cataphoresis apparatus can positively be changed with each other. Particularly, the current polarity can positively be changed to the polarity opposite to that of the last migration at the time of cutting off the power supply even the power supply is once cut off and the next migration is begun.

What is claimed is:

1. A device for automatically changing the polarity of a direct current supply source for use in a cataphoresis apparatus including a migration time setting section, a migration current generator connected to said section and having two output terminals for delivering migration current of positive and negative polarities and a migration cell connected to the migration current generator, the device comprising a polarity change switch connected between the migration current generator and the migration cell for changing the polarity of migration current, means connected to the migration time setting section for generating a functional signal in response to detection of an instruction signal from the migration setting section, signal processing means connected to the generator for processing the functional signal to finally drive the polarity change switch, and polarity changing and memorizing means connected between ground and the polarity change switch and between said signal processing means and a voltage supply source for instructing polarity change of the migration current to the polarity change switch and for memorizing the changed polarity of the migration current in spite of switching on or off of a power supply source, said polarity changing and memorizing means changing the polarity of the migration current to a polarity opposite to the just previous polarity every detection of the instruction signal from the migration time setting section and holding the changed polarity until a next instruction signal is received.

2. An automatic polarity changing device as claimed in claim 1, wherein said signal processing means comprises a signal generator connected to the function signal generator for generating a gating signal, a D flip-flop having a first D terminal connected to said supply source, a second terminal connected to the output of the generator and having output terminals, two AND gates each having two inputs and one output, one of each input being connected to said output terminals of the flip-flop respectively, the other of each input being connected to the signal generator, and two transistors each having base electrode connected to the output of the AND gates, emitter electrode connected to ground and collector electrode connected to coils of said polarity changing and memorizing means, respectively.

3. An automatic polarity changing device as claimed in claim 2, wherein said polarity changing and memorizing means comprises a relay connected to the transistors of said signal processing means for mechanically memorizing the current polarity in the previous migration even if a power source is cut off in response to switching off and on the supply source.

4. An automatic polarity changing device as claimed in claim 3, wherein the relay comprises two coils connected to the collectors of the transistors, respectively, and one contact connected to the polarity change switch and the D terminal of the flip-flop and between supply source and ground.

5. A device for automatically changing the polarity of a direct current supply source for use in a cataphoresis apparatus including a migration time setting section, a migration current generator connected to said section and having two output terminals for delivering migration current of positive and negative polarities and a migration cell connected to the migration current generator, the device comprising means connected to the migration time setting section for generating a functional signal in response to detection of an instruction signal from the section, a transistor having a base electrode connected to the functional signal generator, emitter electrode connected to ground and collector electrode, a coil connected between a voltage supply source and the collector electrode of the transistor and a rotary solenoid connected between said supply source and ground and electromagnetically coupled to the coil, said rotary solenoid having an output connected to the polarity change switch so as to change the polarity of the migration current to a polarity opposite to the just previous polarity every detection of an instruction signal from the migration time setting section and holding the changed polarity until next instruction signal is received.

* * * * *